(12) United States Patent
Carlisle et al.

(10) Patent No.: US 8,876,756 B2
(45) Date of Patent: Nov. 4, 2014

(54) PORTABLE INFUSION MANAGEMENT APPARATUS AND METHOD

(75) Inventors: Jeffrey A. Carlisle, Stratham, NH (US); Benjamin G. Powers, Portsmouth, NH (US)

(73) Assignee: Ivenix, Inc., Amesbury, MA (US)

(*) Notice: Subject to any disclaimer, the term of this patent is extended or adjusted under 35 U.S.C. 154(b) by 289 days.

(21) Appl. No.: 13/207,515

(22) Filed: Aug. 11, 2011

(65) Prior Publication Data

US 2012/0041413 A1    Feb. 16, 2012

Related U.S. Application Data

(60) Provisional application No. 61/372,557, filed on Aug. 11, 2010.

(51) Int. Cl.
*A61M 31/00* (2006.01)
*A61M 5/168* (2006.01)
*A61M 5/155* (2006.01)

(52) U.S. Cl.
CPC ....... *A61M 5/16881* (2013.01); *A61M 2205/50* (2013.01); *A61M 2205/3368* (2013.01); *A61M 5/155* (2013.01)

USPC ................................. 604/66; 604/67; 604/500

(58) Field of Classification Search
USPC ................................. 604/66, 67, 500
See application file for complete search history.

(56) References Cited

U.S. PATENT DOCUMENTS

| 6,280,408 B1* | 8/2001 | Sipin ............................... 604/65 |
| 2002/0156464 A1* | 10/2002 | Blischak et al. ........... 604/892.1 |
| 2009/0026146 A1* | 1/2009 | Carlisle et al. ................ 210/741 |
| 2010/0309005 A1* | 12/2010 | Warner et al. ................ 340/606 |

* cited by examiner

*Primary Examiner* — Edelmira Bosques
(74) *Attorney, Agent, or Firm* — Chapin IP Law, LLC

(57) ABSTRACT

A portable infusion apparatus and method are provided for controlling the delivery of medicinal fluid to a patient. A fluid delivery system receives control input to control a setting of a variable fluid flow resistor. The variable fluid flow resistor resists passage of fluid through a fluid pathway between a fluid source and a recipient. The fluid delivery system: produces a control signal indicative of the setting of the variable fluid flow resistor; derives a fluid flow rate value from the control signal; and applies pressure to the fluid source to deliver the fluid from the fluid source to the recipient through the variable fluid flow resistor at a rate as specified by the derived fluid flow rate value.

25 Claims, 4 Drawing Sheets

PORTABLE INFUSION MANAGEMENT APPARATUS AND METHOD

CROSS-REFERENCE TO RELATED APPLICATION

This application claims the benefit of priority under 35 U.S.C. §119(e) based on U.S. Provisional Application No. 61/372,557 filed Aug. 11, 2010. The aforementioned application is incorporated herein by reference in its entirety.

BACKGROUND

The present disclosure relates to fluid flow control devices and more particularly to portable infusion pumps.

The primary role of an intravenous (IV) infusion device has been traditionally viewed as a way of delivering IV fluids at a certain flow rate. In emergency situations, such as natural disasters, industrial accidents, traffic accidents, police or battlefield actions, the best outcomes for trauma victims occur when an IV can be administered to prevent shock and stabilize the patient for transport to a medical facility. In practice, the limited battery function, the large size and the complexity of modern pumps has required first responders to rely on gravity infusions or delay in starting an infusion until the patient is safely inside a secure care area. This delay in providing fluids and medicine increases the mortality risk for those needing care, and gravity infusions are inconsistent at best in transport situations, sometimes running faster, sometimes slower, and sometimes not at all depending on the relative height of the fluid source and the patient's systolic blood pressure. Clearly then, there is a need for a portable pump that can be used by people with only limited training in trauma situations. Such a pump would allow greater control of infusions that are currently delayed or set and run as gravity infusions and subject to the variability of gravity infusion during patient transport and would add a significant level of safety and benefit to trauma patients, helping to stabilize them during transport to a secure care area.

In clinical practice, it is common to have fluid delivery goals other than flow rate. For example, it may be important to deliver a certain dose over an extended period of time, even if the starting volume and the actual delivery rate are not specified. This scenario of "dose delivery" is analogous to driving an automobile a certain distance in a fixed period of time by using an odometer and a clock, without regard to a speedometer reading. The ability to perform accurate "dose delivery" would be augmented by an ability to measure the volume of liquid remaining in the infusion.

Flow control devices of all sorts have an inherent error in their accuracy. Over time, the inaccuracy of the flow rate is compounded, so that the actual fluid volume delivered is further and further from the targeted volume. If the volume of the liquid to be infused can be measured, then this volume error can be used to adjust the delivery rate, bringing the flow control progressively back to zero error. The ability to measure fluid volume then provides an integrated error signal for a closed feedback control infusion system.

In clinical practice, the starting volume of an infusion is not known precisely. This is especially true with first responders arriving in a disaster or battlefield situation. The original contained volume is not a precise amount and then various concentrations and mixtures of medications are added. The result is that the actual volume of an infusion may range, for example, from about 5% below to about 20% above the nominal infusion volume. The EMT or other user of an infusion control device is left to play a game of estimating the fluid volume, so that the device stops prior to completely emptying the container, otherwise generating an alarm for air in the infusion line or the detection of an occluded line. This process of estimating often involves multiple steps to program the "volume to be infused." This process of programming is time consuming and presents an unwanted opportunity for programming error. Therefore, it would be desirable if the fluid flow control system could measure fluid volume accurately and automatically.

If the fluid volume can be measured then this information could be viewed as it changes over time, providing information related to fluid flow rates. After all, a flow rate is simply the measurement of volume change over time.

The formulation of the ideal gas law, $PV=nRT$, has been commonly used to measure gas volumes. One popular method of using the gas law theory is to measure the pressure in two chambers, one of known volume and the other of unknown volume, and then to combine the two volumes and measure the resultant pressure. This method has two drawbacks. First the chamber of known volume is a fixed size, so that the change in pressure resultant from the combination of the two chambers may be too small or too large for the measurement system in place. In other words, the resolution of this method is limited. Second, the energy efficiency of this common measurement system is low, because the potential energy of pressurized gas in the chambers is lost to the atmosphere during the testing. The present invention contemplates an improved volume measurement system and method and apparatus that overcome the aforementioned limitations and others.

SUMMARY

In one aspect, a method and apparatus for determining fluid flow rate over an extended period of time are provided.

In another aspect, a method and apparatus for determining fluid flow rate over a relatively short period of time are provided.

One advantage of the presently disclosed portable infusion device over most alternate infusion means is that it does not require being hung above the patients head. Most alternate infusion means rely at least in part on the pressure head created by suspending the fluid source above the patient. Suspending the fluid a distance above the device and the patient helps fill the pumping segment or chamber or alternate embodiments and deviations from the expected pressure head generated by suspending the fluid above the patient affects the flow rate accuracy of the device. In situations such as would be experienced by a first responder to an accident or disaster or a medic attending to and evacuating wounded, suspending the fluid source above the patient is often inconvenient or impossible. In those situations, delivery of fluid to stabilize and maintain patients in transit can be variable, putting patients at risk. Since the preferred embodiment of the device herein described generates all the pressure required for delivering the fluid, the system is indifferent to the relative height of the device to the patient. An infusion can be started with this device and then the device can be secured to the patient, which makes transporting the patient in difficult circumstances simpler.

Another advantage of the presently disclosed portable infusion device is found in that the pressure measurements made over time can be used to accurately compute fluid flow rate.

Another advantage of the present portable infusion device and method is found in that pressure measurements may be made using an inexpensive and simple pumping mechanism.

Another advantage of the present portable infusion device and method is found in that pressure measurements may be made without significant loss of energy.

Another advantage of the present portable infusion device and method is found in that pressure measurements may be made over a wide range of volumes.

Another advantage of the present portable infusion device and method of this disclosure is that its simplicity, along with feedback control, makes for a reliable architecture.

Still further features and advantages of the present portable infusion device in accordance with the present disclosure will become apparent to those skilled in the art upon a reading and understanding of the following detailed description, which serves to illustrate by way of example the principles of the invention and is not intended to limit the invention.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
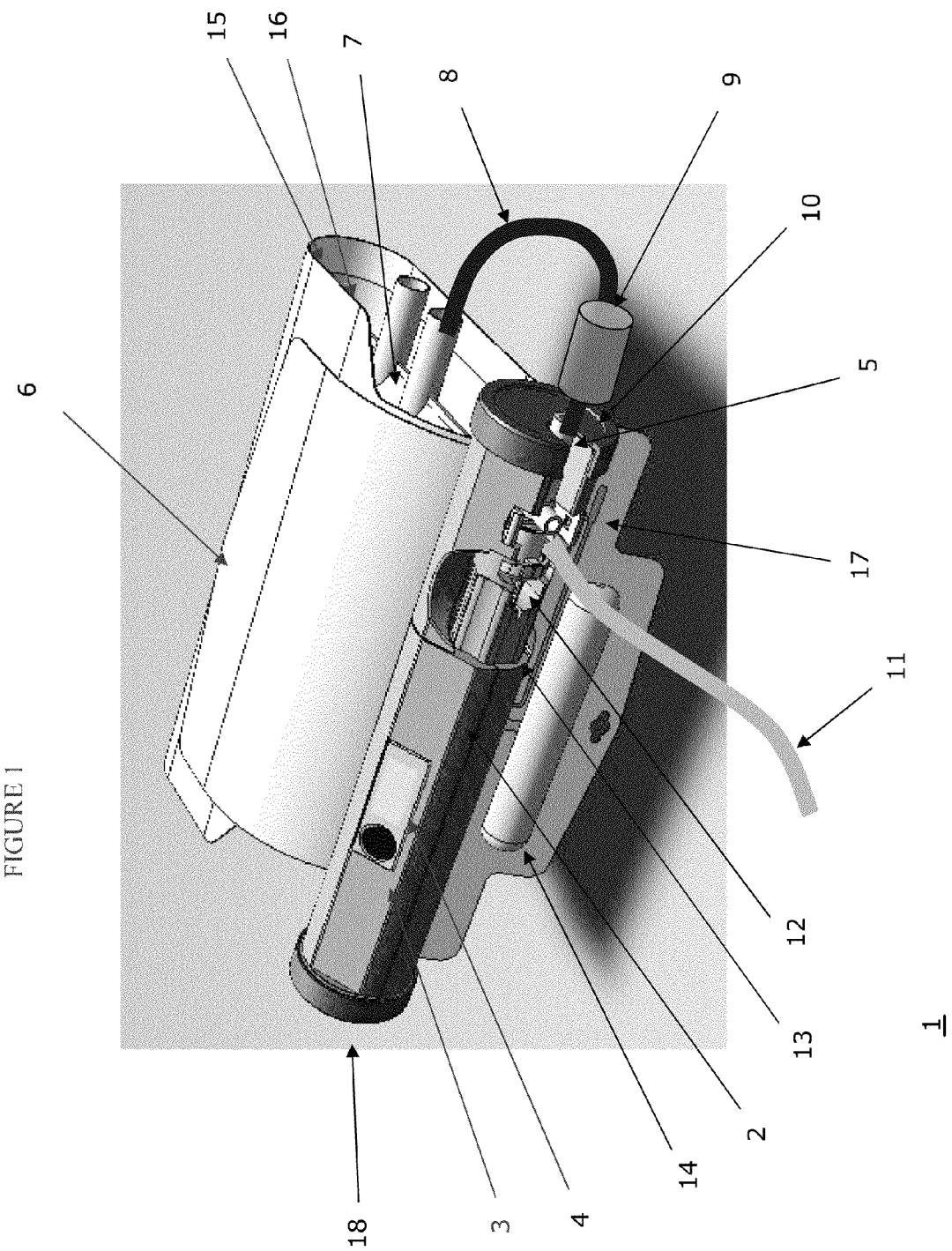
FIG. 1 is a perspective view of an infusion pump in accordance with an exemplary embodiment.

Referring to the drawings, wherein like reference numerals are used to indicate like or analogous components throughout the several views, FIG. 1 depicts an exemplary infusion system 1 in accordance with an exemplary embodiment of the present invention. The system includes a housing 2 that contains a power supply 21 and associated electronics. The housing 2 connects to an administration cuff 6 and interfaces with a variable fluid flow resistor 5. The variable flow fluid resistor 5 includes a cap 12, which snaps into a pocket containing a potentiometer (not shown), such that the cap 12 and potentiometer turn together. An actuator 13 is rotatably coupled to the housing 2 and includes a shaft which interfaces with a potentiometer. Rotation or twisting of the actuator 13 rotates the cap 12 of the variable fluid flow resistor 5 and the potentiometer provides an indication of the rotational position of the resistor cap 12.

The administration cuff 6 includes an inflatable bladder 16. The administration cuff 6 is wrapped around a fluid source 7 comprising a flexible bag containing the fluid to be infused. It will be recognized that the IV fluid to be delivered may be any medicinal fluid, intravenous solution, blood product, or the like, and the term medicinal fluid, IV fluid, etc., may be used herein interchangeably without regard to nuances in meaning. The cuff 6 also includes a structural element 15 disposed about the inflatable bladder 16. Similar to a blood pressure cuff, the administration cuff 6 can be wrapped around flexible fluid source bags 7 of a variety of sizes. The flap 26 is securely closed via one or more fasteners (not shown), e.g., hook and loop fastener, incorporated into the structural element 15 of the cuff 6. One skilled in the art can envision variations on this theme and cuffs made from woven fabric as well as from flexible plastic film. Closures allowing adjustment of the cuff 6 can include the mentioned hook and loop as well as, snaps, post and eye fasteners, and a variety of other embodiments. The fasteners may allow for the adjustment of the cuff 6 and may be incorporated into the outer, structural portion 15 of the cuff 6. These variations are all within the spirit of the invention and included herein.

A disposable administration set 8 connects to the outlet of the fluid source 7 and includes an air eliminating filter 9, the variable fluid flow resistor 5, and the line to the patient 11, e.g., which in turn may be coupled to or include an IV catheter or cannula (not shown), as generally known in the art. The administration cuff 6 also includes a calibration tank 14 of known volume, a temperature sensor such as thermistor 17, and the plumbing and electrical means to connect the calibration tank 14 to the pressure source within the housing 2 and to the bladder 16; and to connect the thermistor 17 to the controls within the housing 2. The housing 2 includes a user interface, such as an ON/OFF button 3 and a user display 4. The display 4 may be an LCD display, LED display, etc. The housing 2 has two end caps 10 and 18, which connect securely to the housing 2 and act to contain and protect the electronics, power supply 21, and pressure system enclosed within the housing 2.

Figure 2:
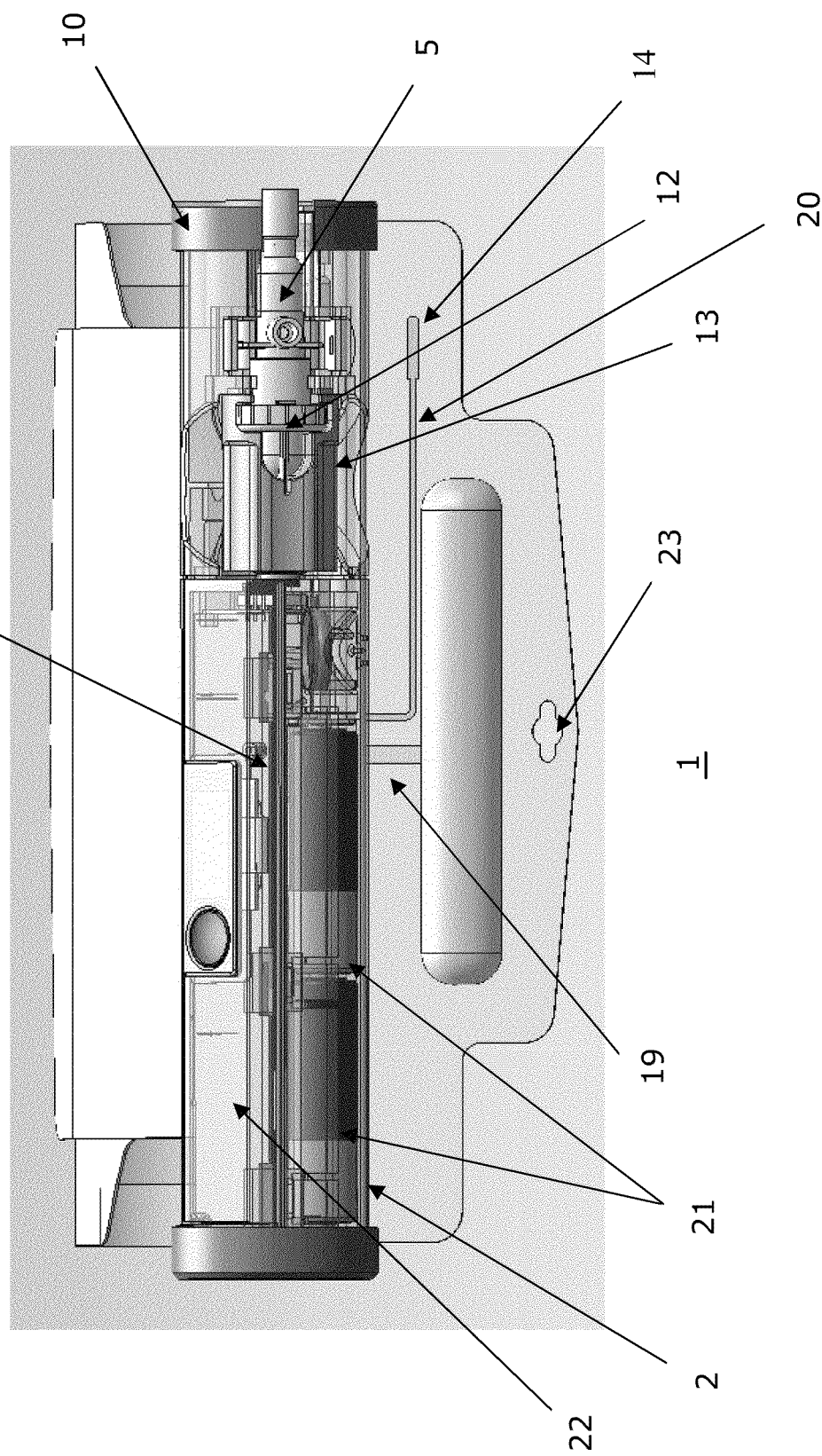
FIG. 2 is a perspective view of an infusion pump in accordance with the exemplary embodiment appearing in FIG. 1, with the housing cover removed for ease of exposition.

Referring now to FIG. 2; in this view, the housing 2 is shown transparent to aid in the description of the device, and the tubes 8 and 11 and the air eliminating filter 9 have been omitted for clarity. In this view, the relation of the variable fluid flow resistor 5 to the potentiometer is more clearly seen. The variable flow resistor 5 snaps into the housing 2, the cap 12 of the variable flow resistor 5 being captured by a pocket in the potentiometer actuator 13. A protrusion such as a fin on the cap 12 of the variable flow resistor 5 fits into a complimentary, aligned slot or opening in the potentiometer actuator 13, assuring that the resistor 5 can only be inserted when the resistor is closed position (preventing unintended flow), and enabling the cap and the potentiometer to turn together. The potentiometer actuator 13 may have a fluted exterior to enable the element to be turned like a thumb wheel. It is recessed in the housing to prevent inadvertent adjustment.

Also seen in this view are the batteries 21, the electronic control board 22 and the hanging hole 23 that is part of the administration cuff 6. The plumbing connection 19 from the known volume 14 to the plumbing manifold with the housing 2 and the electrical connection 20 from the thermistor 14 to the controls within the housing 2 are also more clearly seen in this view. The portable infusion device 1 is powered by a power supply 21 and is controlled by an electronic control board 22. In the illustrated embodiment the power supply 21 consists of two batteries, however other power supplies such as one or more batteries or battery packs are contemplated. The hanging hole 23 on the cuff 6 provides a means for hanging the infusion device 1 when necessary such as during an infusion or for storage. The calibration tank 14 is connected to the plumbing manifold (not shown) within the housing 2 by a connection 19. The thermistor 17 is connected to control board 22 within the housing 2 by an electrical connection 20.

The control board 22 includes a processing unit, such as a microprocessor, microcontroller, an (optionally programmable) controller, embedded controller, or alternately (and providing the equivalent functionality) a finite state machine, e.g., which may be realized by a programmable logic device (PLD), field programmable gate array (FPGA) or field programmable object array (FPOA).

Figure 3:
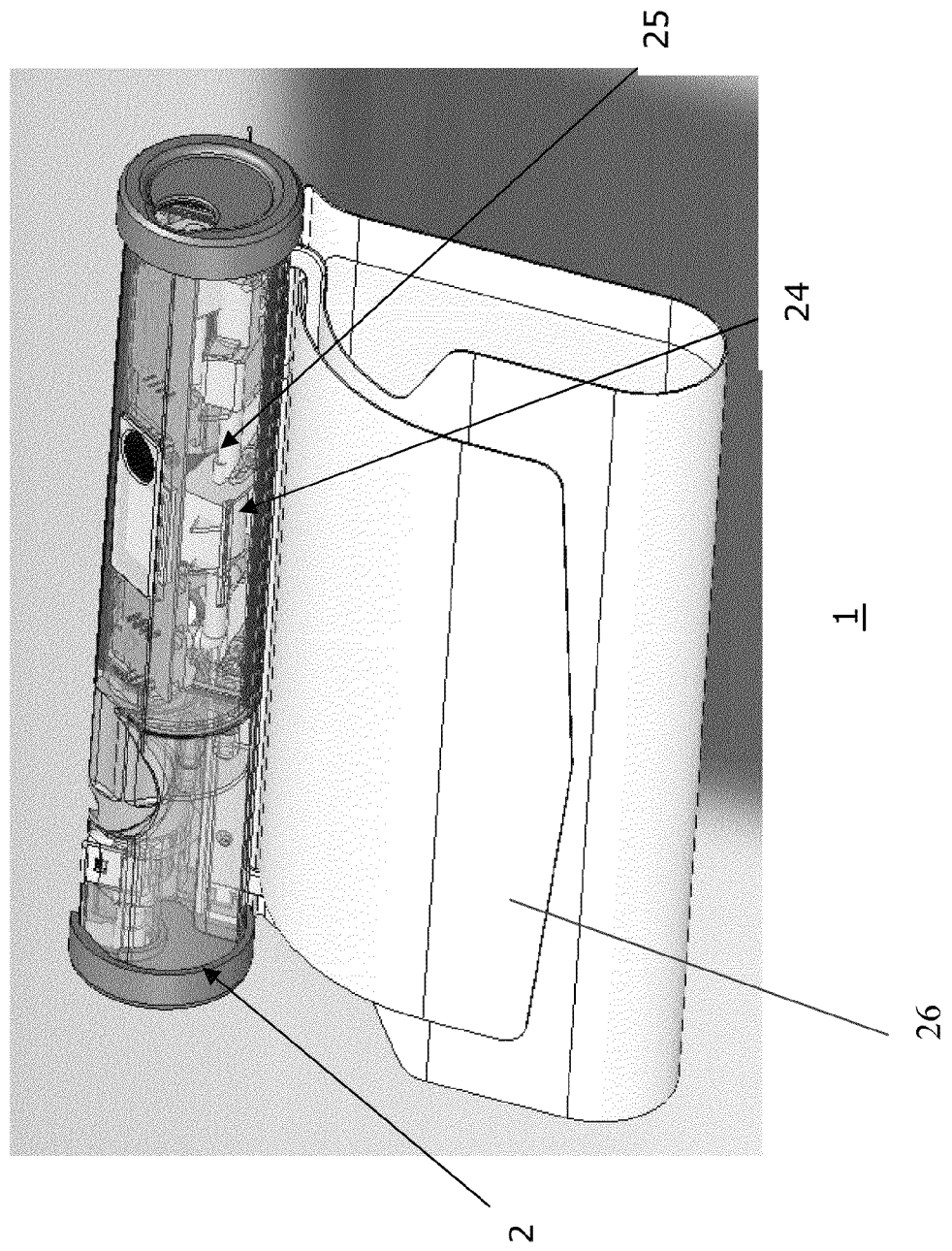
FIG. 3 is a top perspective view of the infusion pump embodiment of FIG. 1, wherein the housing cover has been removed.

Referring now to FIG. 3; in this view, the housing 2 is shown transparent to aid in the description of the device, and the tubes 8 and 11 and the air eliminating filter 9 have been omitted for clarity. In this view, a pump 24 and an internal plumbing manifold 25 can be seen within the housing 2.

In preparation for using a device according to the preferred embodiment to deliver an infusion to a patient or subject, a user would connect the disposable tube set 8 to the flexible bag 7 containing the fluid to be infused. Typically, this is accomplished by including a spike fitting (not shown) on the end of the disposable tube set 8 and pushing that through a pierceable membrane that is molded into the flexible bag for this purpose. There are other configurations that would also work to connect the tube set 8 to the bag, as are known to persons skilled in the art, such as the use of male and female luer connectors on the bag and the tube set. The user would then open the variable flow fluid resistor by turning the cap 12 counter clockwise and prime the tube set 8 with fluid from the flexible bag, being careful to fully wet the air elimination filter 9 and displace all air from the tube set 8 with the fluid to be infused. Closing the variable flow resistor—e.g., by turning the cap 12 clockwise in the illustrated preferred embodiment—is sufficient to keep fluid from flowing from the primed tube set 8 in an uncontrolled manner.

Subsequent to connecting and priming the tube set 8, the user places the flexible fluid source 7 in the administration cuff 6, then pulls on the flap 26 of the cuff 6 to remove all slack, and closes the open end of the cuff with the hook and loop (or other) fastener. Friction between the flexible bag 7 and the inside of the administration cuff 6 prevents bag movement. The variable resistor 5 is snapped into the potentiometer actuator 13, and the cap 12 is captured by the actuator such that the cap 12 can turn and open the variable fluid flow resistor 5 only by rotating the actuator 13 of the potentiometer.

Once the fluid flow resistor 5 is in place the user, e.g., a nurse, doctor, EMT, or other medically trained professional, turns the portable infusion system 1 on using the ON/OFF button 3 if the device were not already on. When the portable infusion system 1 is ready for programming, the volume rate visible on the display 4 will show display zero. The fluid outlet 11 of the disposable tube set 8 is then connected to the vasculature of the patient. The infusion is then started by the user rotating the potentiometer actuator 13 using a finger or thumb through the aligned opening in the housing 2 provided. The user turns the actuator 13 to the desired infusion rate. The infusion is then started by the user twisting the actuator 13—where the variable flow resistor 5 is located—holding the fixed housing 2. As the actuator 13 is rotated, the cap 12 of the variable resistor 5 is turned, opening the variable resistor 5. The potentiometer is also rotated simultaneously, providing feedback to the control board 22, e.g., by providing a control signal to the control board representative of the amount that the variable fluid flow resistor 5 has been opened. The display 4 will update as the actuator 13 is turned, showing an infusion rate. The user stops turning the potentiometer when the desired flow rate is displayed on the display 4. The act of turning the actuator not only rotates the potentiometer to set the desired infusion rate, but also rotates the cap 12 to open the variable resistance valve 5 to the appropriate location to enable the infusion at the desired rate. When the potentiometer stops changing (i.e., when the user sees the desired flow rate displayed and stops turning the actuator 13), the controller initiates the pressure delivery cycle.

To initiate the pressure delivery cycle, the air pump 24 is turned on and pressurizes the bladder 16 surrounding the fluid 7 to be delivered. The bladder 16 is pressurized to an initial pressure. A pressure sensor, transducer, etc., is provided within the manifold 25 for indicating the actual pressure in the bladder 16, e.g., by providing a voltage signal representative of the actual pressure in the bladder 16 to the processor on the electronic control board 22. The pump 24 is again activated and the air from the pump 24 is used to pressurize the calibration tank 14 to a higher pressure than the bladder. Again, a pressure sensor within the manifold 25 indicating the actual pressure within the calibration tank 14, and providing a voltage signal representative of the actual pressure to the processor on the electronic control board 22. The pump 24 is then turned off and a valve in the manifold 25 is opened, fluidically connecting the calibration chamber 14 to the bladder 16. The resulting pressure in the combined volume is measured by a pressure sensor within the manifold 25 indicating the actual pressure, and providing a voltage representative of the actual pressure of the combined volume to the processor on the electronic control board 22.

Figure 4:
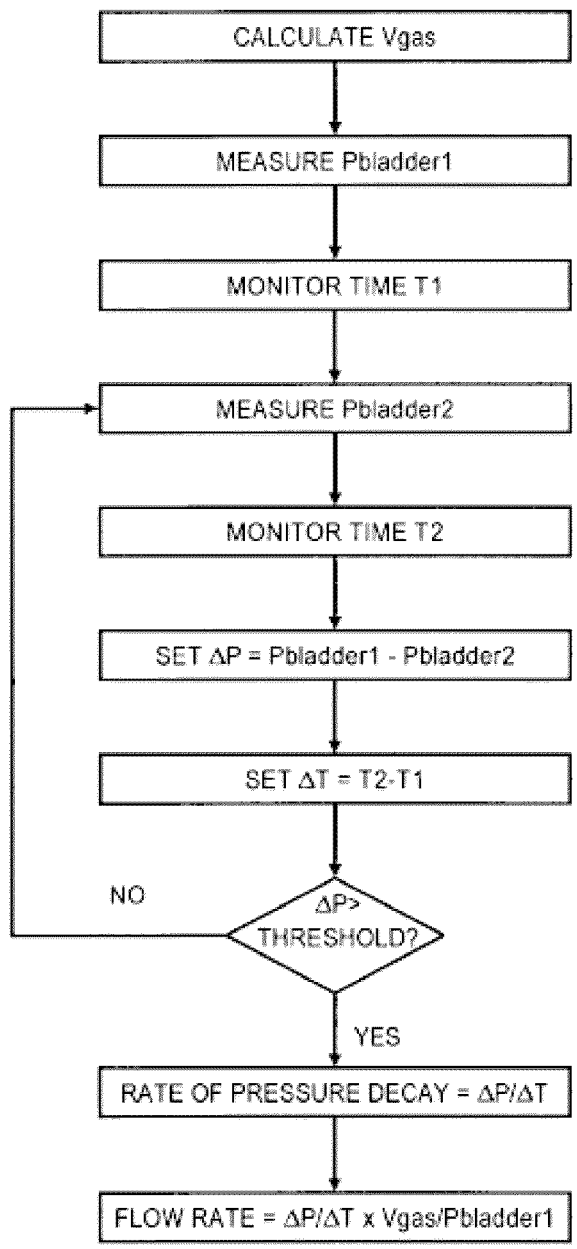
FIG. 4 is a flow chart outlining an exemplary method of calculating flow rate based on pressure decay.

The three pressure signals obtained as described above and the known volume of the calibration tank 14 provide sufficient information to determine the volume of air in the bladder 16. As fluid flows from the fluid source 7, the volume of the fluid leaving the fluid source 7 is filled by the bladder 16 resulting in a lower pressure within the bladder volume. Since the initial volume of air within the bladder 16 was known, measuring the pressure decay in the bladder 16 volume indicates the flow rate of the fluid from the fluid source 7. If the flow from the fluid source 7 measured in this manner is not equal to the desired volume entered at the start of the infusion, the system increases the pressure in the bladder 16 for flow rates less than the desired flow rate, and vents pressure from the bladder 16 (through a valve located within the manifold assembly 25) for flow rates higher than the desired flow rate. Throughout the fluid delivery process, this sequence of events is repeated to verify the volume of air in the bladder 16 and monitor and adjust the pressure decay as a measure of flow rate. FIG. 4 shows a flow chart illustrating this delivery process.

Since the Pressure/Volume curve of a gas is influenced by changes in temperature as described in Boyle's Laws, the processor on the electronic control board 22 monitors the temperature of the system as indicated by the thermistor 17 and adjusts the calculated flow rate accordingly.

It can be now be seen that the preferred embodiment described provides a simple device that can accurately deliver a fluid to a patient quickly and accurately, requiring few steps to start by first responders or medics, requires only minimal training and delivers fluid independently of the fluid source height in relation to the patient.

While there has been shown and described what is considered to be the presently preferred embodiments of the invention, it will of course, be understood that various modifications and changes in form or detail could readily be made without departing from the spirit of the invention. It is therefore intended that the invention not be limited to the exact forms described and illustrated, but should be construed to cover all such modifications and alterations that may fall within the scope of the appended claims and their legal equivalents.

What is claimed is:
1. A method comprising:
receiving control input inputted to a fluid delivery system, the control input controlling a position setting of a variable fluid flow resistor, the variable fluid flow resistor resisting passage of fluid through a fluid pathway between a fluid source and a recipient;

producing a control signal indicative of the position setting of the variable fluid flow resistor;

deriving a fluid flow rate value from the control signal;

applying pressure to the fluid source to deliver the fluid from the fluid source to the recipient through the variable fluid flow resistor at a rate as specified by the derived fluid flow rate value; and wherein producing the control signal includes: physically detecting the position setting of the variable fluid flow resistor using a position sensor coupled to the variable fluid flow resistor, the position sensor physically detecting a degree to which the variable fluid flow resistor is open, the position sensor producing the control signal.

2. The method as in claim 1, wherein the control input is a single physical control action inputted by a user, the single physical control action simultaneously: i) controlling the position setting of the variable fluid flow resistor and ii) resulting in generation of the control signal indicative of a position of the variable fluid flow resistor.

3. The method as in claim 1 further comprising:
initiating display of the derived fluid flow rate value on a display screen for viewing by a used operating the fluid delivery system, a magnitude of the derived fluid flow rate value as displayed on the display screen varying depending on the position setting of the variable fluid flow resistor.

4. The method as in claim 1 further comprising:
receiving the control input at an input apparatus physically controlled by a user, the input apparatus mechanically controlling the position setting of the variable fluid flow resistor in accordance with the control input; and the input apparatus including the position sensor, the position sensor physically detecting the position setting of the variable fluid flow resistor and producing the control signal based on the detected position setting.

5. The method as in claim 1 further comprising:
measuring the pressure applied to the fluid source;

from the measured pressure, calculating an actual flow rate of the fluid passing from the fluid source through the variable fluid flow resistor to the recipient; and increasing the pressure applied to the fluid source in response to detecting that the actual flow rate is less than the derived flow rate value.

6. The method as in claim 1 further comprising:
measuring the pressure applied to the fluid source to calculate an actual flow rate of the fluid passing from the fluid source through the variable fluid flow resistor to the recipient; and decreasing the pressure applied to the fluid source in response to detecting that the actual flow rate is greater than the derived flow rate value.

7. The method as in claim 1 further comprising:
controlling an actual flow rate of the fluid delivered from the fluid source through the fluid pathway based on control of the pressure and the position setting of the variable fluid flow resistor.

8. The system as in claim 1, wherein the control signal indicates a fluid flow restriction setting of the variable fluid flow resistor, the control signal being feedback from the position sensor that monitors a position of the variable fluid flow resistor.

9. The method as in claim 1, wherein the fluid source is a first chamber in an enclosure, the first chamber containing the fluid, the enclosure including a second chamber, the method further comprising:
pumping a gas into the second chamber, the pumped gas in the second chamber exerting the pressure on the first chamber and causing the fluid in the fluid source to flow through the variable fluid flow resistor to the recipient at the derived flow rate.

10. The method as in claim 9 further comprising:
monitoring a first pressure representing a pressure of the gas pumped into the second chamber;

monitoring a second pressure representing a pressure of gas in a calibration tank, the calibration tank having a known volume;

subsequent to opening a valve disposed between the second chamber and the calibration tank, monitoring a third pressure representing pressure in a combined volume including the second chamber and the calibration tank; and calculating a volume of air in the second chamber based on the first monitored pressure, the second monitored pressure, and the third monitored pressure.

11. The method as in claim 10 further comprising:
repeatedly calculating the volume of the air in the second chamber based on the first monitored pressure, the second monitored pressure, and the third monitored pressure; and utilizing the repeatedly calculated volume of air in the second chamber as a basis to determine an actual flow rate of delivering the fluid from the fluid source through the variable fluid flow resistor to the recipient.

12. The method as in claim 10 further comprising:
calculating an actual flow rate of fluid through the variable fluid flow resistor based on measurements of the pressure applied to the fluid source.

13. The method as in claim 10 further comprising:
measuring a decay of the pressure in the second chamber; and calculating a flow rate of fluid through the variable fluid flow resistor to the recipient based on an initial calculated volume in the second chamber and the measured decay of the pressure in the second chamber.

14. The method as in claim 13 further comprising:
adjusting the actual flow rate based on a measured temperature.

15. A system comprising:
an input device that receives control input, the control input physically controlling a position setting of a variable fluid flow resistor, the variable fluid flow resistor disposed in a fluid pathway between a fluid source and a recipient;

a position sensor coupled to the variable fluid flow resistor, the position sensor monitoring the variable fluid flow resistor and physically detecting a degree to which the variable fluid flow resistor is open, the position sensor producing a control signal indicative of the position setting of the variable fluid flow resistor; and a flow controller configured to receive the control signal, the flow controller: i) deriving a fluid flow rate setpoint from the control signal, and ii) initiating application of pressure to the fluid source to deliver the fluid from the fluid source to the recipient through the variable fluid flow resistor at the derived fluid flow rate setpoint.

16. The system as in claim 15, wherein the control input is a single control action inputted by a user, the single control action simultaneously: i) controlling the position setting of the variable fluid flow resistor and ii) resulting in generation of the control signal representative of a position of the variable fluid flow resistor.

17. The system as in claim 15 further comprising:
a display screen, the display screen displaying the derived fluid flow rate setpoint for viewing by a user, a magnitude of the derived fluid flow rate setpoint as displayed on the display screen varying depending on the position setting of the variable fluid flow resistor.

18. The system as in claim 15, wherein the flow controller:
utilizes a measure of the pressure applied to the fluid source to calculate an actual flow rate of the fluid passing from the fluid source through the variable fluid flow resistor to the recipient; and
increases the pressure applied to the fluid source in response to detecting that the calculated actual flow rate is less than the derived fluid flow rate setpoint.

19. The system as in claim 15, wherein the flow controller:
utilizes a measure of the pressure applied to the fluid source to calculate an actual flow rate of the fluid passing from the fluid source through the variable fluid flow resistor to the recipient; and
decreases the pressure applied to the fluid source in response to detecting that the calculated actual flow rate is greater than the derived fluid flow rate setpoint.

20. The system as in claim 15, wherein the flow controller:
controls an actual flow rate of the fluid delivered from the fluid source through the fluid pathway based on controlling a magnitude of the pressure and the position setting of the variable fluid flow resistor.

21. The system as in claim 15, wherein the fluid source is a first chamber in an enclosure, the first chamber containing the fluid, the enclosure including a second chamber, the system further comprising:
a pump configured to pump a gas into the second chamber, the pumped gas in the second chamber causing exertion of the pressure on the first chamber and causing the fluid in the fluid source to flow through the variable fluid flow resistor to the recipient at the derived fluid flow rate setpoint.

22. The system as in claim 21, wherein the flow controller:
monitors a first pressure representing a pressure of the gas pumped into the second chamber;
monitors a second pressure representing a pressure of gas inputted to a calibration tank, the calibration tank having a known volume;
subsequent to opening a valve coupling the second chamber and the calibration tank, monitors a third pressure representing a pressure in a combined volume including the second chamber and the calibration tank; and
calculates a volume of air in the second chamber based on the first pressure, the second pressure, and the third pressure.

23. The system as in claim 22, wherein the flow controller:
repeatedly calculates the volume of the air in the second chamber based on the first monitored pressure, the second monitored pressure, and the third monitored pressure; and
utilizes the repeated calculated volume of air in the second chamber as a basis to determine an actual flow rate of delivering the fluid from the fluid source through the variable fluid flow resistor to the recipient.

24. The system as in claim 22, wherein the flow controller:
measures a decay of the pressure in the second chamber; and
calculates a flow rate of fluid through the variable fluid flow resistor to the recipient based on an initial calculated volume in the second chamber and the measured decay of the pressure in the second chamber.

25. The system as in claim 24, wherein the flow controller:
adjusts the calculated flow rate based on a measured temperature.

* * * * *